(12) United States Patent
Yamaguchi et al.

(10) Patent No.: US 8,241,683 B2
(45) Date of Patent: Aug. 14, 2012

(54) DECOLONIZING AGENT FOR HELICOBACTER PYLORI

(75) Inventors: Kikuji Yamaguchi, Atami (JP); Toru Kono, Asahikawa (JP)

(73) Assignee: Kikuji Yamaguchi, Atami-shi (JP)

( * ) Notice: Subject to any disclaimer, the term of this patent is extended or adjusted under 35 U.S.C. 154(b) by 391 days.

(21) Appl. No.: 12/596,084

(22) PCT Filed: Apr. 15, 2008

(86) PCT No.: PCT/JP2008/057311
§ 371 (c)(1),
(2), (4) Date: Oct. 15, 2009

(87) PCT Pub. No.: WO2008/133098
PCT Pub. Date: Nov. 6, 2008

(65) Prior Publication Data
US 2010/0129462 A1    May 27, 2010

(30) Foreign Application Priority Data
Apr. 16, 2007  (JP) ................................ 2007-107113

(51) Int. Cl.
*A61K 36/00*    (2006.01)
(52) U.S. Cl. ........................................ 424/778; 424/725
(58) Field of Classification Search ........................ None
See application file for complete search history.

(56) References Cited

U.S. PATENT DOCUMENTS

| | | | |
|---|---|---|---|
| 6,956,144 B2 * | 10/2005 | Molan | 602/48 |
| 2004/0258765 A1 * | 12/2004 | Gee | 424/539 |
| 2007/0207215 A1 * | 9/2007 | Abashidze et al. | 424/539 |
| 2008/0292715 A1 * | 11/2008 | Snow et al. | 424/539 |
| 2010/0028408 A1 * | 2/2010 | Vandeputte | 424/443 |
| 2011/0038945 A1 * | 2/2011 | Gear | 424/537 |

FOREIGN PATENT DOCUMENTS

| | | | |
|---|---|---|---|
| CN | 1253722 | * | 5/2000 |
| CN | 1411740 | * | 4/2003 |
| CN | 1411740 A | | 4/2003 |
| CN | 1530027 | * | 9/2004 |
| KR | 2003-0034290 A | | 5/2003 |

OTHER PUBLICATIONS

Bansal et al. Honey—A Remedy Rediscovered and its Therapeutic Utility. Kathmandu Univ. Med. J. 2005. vol. 3, No. 3, Issue 11 pp. 305-309.*
The Chunichi Shimbun, Collecting from medicinal plants, Feb. 17, 2007, Evening paper p. 8. (with English translation).
Nihon Shokuryo Shimbun, Japan Royal Jerry Co, Ltd. develops 10 Yakumitsu Honpo honey products, sets up subsidiary and sells the products, Dec. 6, 2004. (with English translation).
Hyakusai Genki Shimbun, JRJ Seiyaku "Yakumitsu Honpo honey products", Jan. 10, 2005. (with English translation).
Takahashi, "Specific properties of Manuka honey", Honeybee Science, Feb. 25, 2003, vol. 24, No. 1, pp. 7-14. (with English translation).
Kucuk et al., "Biological activities and chemical composition of three honeys of different types from Anatolia", Food Chemistry, Jul. 27, 2007, vol. 100, Issue 2, p. 526-534.
Osato et al., "Osmotic Effect of Honey on Growth and Viability of Helicobacter pylori", Digestive Diseases and Sciences, Mar. 1999, vol. 44, No. 3, pp. 462-464.
Somal et al., "Susceptibility of Helicobacter pylori to the antibacterial activity of manuka honey", Journal of the Royal Society of Medicine, Jan. 1994, vol. 87, No. 1, p. 9-12.

* cited by examiner

*Primary Examiner* — Christopher R. Tate
(74) *Attorney, Agent, or Firm* — Birch, Stewart, Kolasch & Birch, LLP

(57) ABSTRACT

The invention provides a decolonizing agent that can effectively decolonize *Helicobacter pylori*. The decolonizing agent for *Helicobacter pylori* contains *Elsholtzia rugulosa* hemsl honey as an active ingredient.

12 Claims, No Drawings ical field

The invention relates to a decolonizing agent for *Helicobacter pylori*, which can effectively decolonize *Helicobacter pylori* involved in development of peptic ulcer.

BACKGROUND ART

*Helicobacter pylori* is a gram-negative bacillus with a diameter of approximately 0.5 μm and a length of 3-5 μm. *Helicobacter pylori* is a spiral shaped bacterium twisted 2 or 3 times, microscopically observed as an S-shaped bacterium or a winding gull wing-shaped bacterium. *Helicobacter pylori* has 4-8 flagella (called polar flagella) at both ends (poles) of the long axis and can swim and move in a solution or mucous by rotational movement of these flagella. *Helicobacter pylori* is a microaerophilic and highly-auxotrophic bacterium that is difficult to isolate and culture. *Helicobacter pylori* can be cultured in a specialized medium under conditions of 5% oxygen concentration and 5-10% carbon dioxide concentration.

*Helicobacter pylori* inhabits the stomach lining of humans. *Helicobacter pylori* is a causative organism of gastritis, gastric ulcer, and duodenal ulcer, and is also considered to be involved in diseases, such as gastric MALT lymphoma, atrophic gastritis, and gastric hyperplastic polyp. Once *Helicobacter pylori* infects the gastric mucosa, it cannot be decolonized and persists in the stomach in spite of strong immunological response against the infection. In addition, very low intragastric pH due to hydrochloric acid inactivates many antibiotics.

For this reason, an antibiotic and a proton pump inhibitor that strongly inhibits gastric-acid secretion are used in combination to decolonize *Helicobacter pylori*. According to the revised guideline for diagnosis and treatment of *Helicobacter pylori* infection of the Japan Society of *Helicobacter* Research as of February 2003, a combination therapy with three agents (proton pump inhibitor+amoxicillin+clarithromycin) administered for one week is of first choice.

However, a very serious problem of increased resistant bacteria due to chronic administration of an antibiotic is concerned. In Japan, clarithromycin-resistant bacteria have increased rapidly since 2004, accounting for 25-30% in 2004 (according to a surveillance by the Japan Society of *Helicobacter* Research), and have increased further in recent years. Reportedly, in cases of infection with resistant bacteria, decolonization rates are decreased markedly and clarithromycin resistance occurs after failure of decolonization. Therefore, an easy and insufficient decolonization therapy is considered to increase the emergence of resistant bacteria. Furthermore, in cases for which a macrolide antibiotic was previously used for a long time, bacteria may have acquired drug resistance against clarithromycin (according to the above-mentioned guideline for diagnosis and treatment of *Helicobacter pylori* infection).

Therefore, development of decolonizing agents of *Helicobacter pylori*, free from these disadvantages, has been waited.

DISCLOSURE OF INVENTION

Problem to be Solved by the Invention

The invention provides a decolonizing agent that can effectively decolonize *Helicobacter pylori*.

Means of Solving the Problems

As a result of keen examination to solve the above problems, the inventors of the present invention found out that *Elsholtzia rugulosa* hemsl honey could effectively decolonize *Helicobacter pylori*, and completed the invention.

Specifically, the invention relates to:
1. a decolonizing agent for *Helicobacter pylori*, comprising *Elsholtzia rugulosa* hemsl honey as an active ingredient,
2. a decolonizing agent described in the above 1, for using to prevent or ameliorate diseases associated with *Helicobacter pylori*,
3. a method for eliminating *Helicobacter pylori*, consisting of drinking and eating the decolonizing agent of the above 1, and
4. a food additive, containing *Elsholtzia rugulosa* hemsl honey, for decolonization of *Helicobacter pylori*.

Effect of the Invention

The decolonizing agent for *Helicobacter pylori* of the invention has an excellent decolonization effect on *Helicobacter pylori* and is highly safe. Furthermore, the decolonization effect can be obtained in a short time. Therefore, it is very useful to decolonize *Helicobacter pylori* and prevent or ameliorate diseases associated with *Helicobacter pylori*.

The decolonizing agent for *Helicobacter pylori* of the invention means a composition that can inhibit proliferation of *Helicobacter pylori* and decolonize *Helicobacter pylori* from the stomach. The decolonizing agent of the invention can be used to prevent or ameliorate diseases associated with *Helicobacter pylori*, specifically, peptic ulcers such as gastric ulcer and duodenal ulcer, gastritis, and gastric cancer.

*Elsholtzia rugulosa* hemsl honey is honey collected from *Elsholtzia rugulosa* Hemsl. *Elsholtzia rugulosa* Hemsl. (Yahashi) is a shrub belonging to Lamiaceae family, which grows naturally in Yunnan province, China. *Elsholtzia rugulosa* Hemsl. is 0.5-1.5 m tall with many branches from a graybrown stem and white, or sometimes pale-yellow or purple, five-lobed bilabiate corolla. Honey collected from *Elsholtzia rugulosa* Hemsl. is characterized in that it coagulates naturally to become a solid substance.

The *Elsholtzia rugulosa* hemsl honey of the invention can be used after purification by a routine method or as a commercial product without modification. The *Elsholtzia rugulosa* hemsl honey can be added to any food materials, e.g., milk, juices of orange, lemon and the like, milk products such as yogurt, and other foods.

The daily intake of *Elsholtzia rugulosa* hemsl honey in adults as the decolonizing agent of the invention routinely ranges from 0.01 to 10.0 g. Normally the concentration of *Elsholtzia rugulosa* hemsl honey in the decolonizing agent changes with its conditions. In solid forms, such as tablet, chewable tablet, granule, and capsule (e.g., hard capsule), it ranges from 10 to 100 weight percent of the total mass. Preferably, it is prepared at a final concentration of 10~100 μg/ml in the stomach.

The decolonizing agent of the invention can take various forms, including solid foods such as tablet, chewable tablet, granule, and capsule (e.g., hard capsule), liquid diets, liquid drinks such as soup, juice, tea, milk drink, fermented milk drink, soymilk, cocoa, and jelly drink, semisolid foods such as pudding and yogurt, bread, noodles such as wheat noodle, confectionery such as cookie, chocolate, candy, and Japanese cracker, dried seasoning powder, and spreads such as butter and jam In addition, the decolonizing agent of the invention can be used as a supplement food or a medical food. Preferably it takes forms that allow continued intake, including but not limited to confectionery, soup, drink, liquid diets, as well as tablet, chewable tablet, granule, and capsule (hard capsule).

Furthermore, various food additives such as nutrients, various vitamins, minerals, food fiber, polyunsaturated fatty acid, stabilizers such as dispersants and emulsifier, sweetener, taste component, and flavor can be blended with the decolonizing agent of the invention. A liquid decolonizing agent can be prepared in a liquid form from the start, or in a powder or paste form to be dissolved in a certain amount of an aqueous liquid.

Since the decolonizing agent of the invention can decolonize gastrointestinal *Helicobacter pylori*, it can be used to prevent or ameliorate diseases associated with *Helicobacter pylori*. The diseases associated with *Helicobacter pylori* include those caused by the presence of gastrointestinal *Helicobacter pylori*. Specifically, peptic ulcers such as gastric ulcer and duodenal ulcer, gastritis, gastric cancer and the like are included (the guideline for diagnosis and treatment of *Helicobacter pylori* infection (revised version), Japan Society of *Helicobacter* Research, 2003). The Japan Society of *Helicobacter* Research published a "guideline for diagnosis and treatment" in June 2000, suggesting that decolonization treatment is indicated for "all *Helicobacter pylori*-positive gastric ulcer and duodenal ulcer."

BEST MODE TO PUT THE INVENTION INTO PRACTICE

The invention is described in detail with the following examples but is not limited thereto.

EXAMPLE

The antibacterial effects of *Elsholtzia rugulosa* hemsl honey on *Helicobacter pylori* were evaluated as follows.
Materials and Methods for the Experiment 1. *Helicobacter pylori* strains (23 strains of clarithromycin-sensitive bacteria and 11 strains of clarithromycin-resistant bacteria) collected from humans (34 individuals) were used. Antibacterial effects on *Escherichia coli* (5 strains), collected from humans (5 individuals) as general bacteria, were also examined. Antimicrobial activity of *Elsholtzia rugulosa* hemsl honey was examined by the paper disc method with the minimum inhibitory concentration (MIC) used as an indicator. The *Elsholtzia rugulosa* hemsl honey (2 lots of Koumitsu (Registered Mark) made in China), a subject of the study, and manuka honey (JRJ Co. Ltd., New Zealand, UMF10+) that has traditionally been considered to have antibacterial effect on *Helicobacter pylori*, a control group, were compared. An antibacterial activity test was conducted single-blindedly. The test was conducted by the paper disc method. Each honey was dissolved in heated water at 40-50° C. A diluted stock solution (at a concentration of 10%) was 10-fold diluted sequentially with sterile water. In addition, to examine the changes in antibacterial activity by heating, a test was also conducted with diluted stock solutions heated at 85° C. for 30 or 60 minutes.

2. A clinical study on manuka honey was conducted in untreated volunteers carrying *Helicobacter pylori*, from whom consents had been obtained after sufficient explanation of the study. A substantial amount of *Elsholtzia rugulosa* hemsl honey (3 or 5 g), dissolved in 150 ml of water, was given 4 times before each meal and sleep, based on the MIC concentration obtained in 1, to conduct a urea breath test every week as a judgment test of *Helicobacter* decolonization.

Experimental Results

1. The results of the antibacterial activity test by the paper disc method demonstrated that growth of all the strains, including clarithromycin-sensitive HP strains (23 strains) and clarithromycin-resistant HP strains (11 strains), was inhibited by both 2 lots of *Elsholtzia rugulosa* hemsl honey and manuka honey at a concentration of 100 µl (10% dilution)/ml in the media. *Elsholtzia rugulosa* hemsl honey had comparable antibacterial activity with that of manuka honey. Bacterial growth inhibitory effect was observed not only for drug-sensitive HP bacteria but also for drug-resistant HP bacteria. *Elsholtzia rugulosa* hemsl honey had no antibacterial effect on *Escherichia coli* at any concentrations. However, manuka honey had at 100 µl (10% dilution)/ml. Even after heating at 85° C. for 30 or 60 minutes, *Elsholtzia rugulosa* hemsl honey and manuka honey showed no change in the antibacterial effect on *Helicobacter pylori*; growth of all the bacteria was inhibited at 100 µl (10% dilution)/ml. The antibacterial effect of manuka honey on *Escherichia coli* diminished.

2. After continuous intake of 12 g of *Elsholtzia rugulosa* hemsl honey (3 g×4 times) daily for 1 week, the bacterial count in the urea breath test was decreased by 50% as compared with that before intake. The urea breath test demonstrated complete decolonization by continuous intake of 20 g daily (5 g×4 times) for 1 week.
Tablet and Capsule 250 g of *Elsholtzia rugulosa* hemsl honey, 580 g of crystalline cellulose, 118 g of reduced maltose, and 12.5 g of pectin as mucopolysaccharide were mixed. To this mixture, 40 g of sucrose fatty acid ester was added and mixed to prepare powder. This powder was compressed with a tableting machine to prepare 500 mg tablets. This powder was filled into No. 2 hard capsules to prepare capsules.
Fermented Milk Drink 800 g of powdered skim milk, 100 g of butter, 25 g of guar gum as mucopolysaccharide, and 150 g of *Elsholtzia rugulosa* hemsl honey were dissolved in 7 kg of hot water (40° C.). Subsequently, hot water (40° C.) was further added to increase the total amount to 10 kg. Yogurt starter culture was added to this solution at 1 percent by mass, followed by agitation at 40° C. to achieve 1% lactic acid degree. When 1% lactic acid degree was achieved, the solution was cooled to 10° C. and packaged into 200 ml each to prepare lactic acid bacteria beverage.

INDUSTRIAL APPLICABILITY

The decolonizing agent for *Helicobacter pylori* of the invention is useful to decolonize *Helicobacter pylori* involved in development of peptic ulcer.

The invention claimed is:

1. A method of treating a subject having a *Helicobacter pylori* infection of the gastric mucosa, the method comprising administering a therapeutic composition comprising an effective amount of *Elsholtzia rugulosa* Hemsl. honey to the subject.

2. The method of claim 1, wherein the therapeutic composition is administered in a daily dose of 0.01 g to 10.0 g.

3. The method of claim 1, wherein the therapeutic composition further comprises at least one of an antibiotic and a proton pump inhibitor.

4. The method of claim 1, wherein the therapeutic composition is added to a food before it is administered to the subject.

5. The method of claim 4, wherein the food is a liquid diet drink, a soup, a juice, a tea, a milk drink, a fermented milk drink, soymilk, cocoa, a jelly drink, a pudding, a yoghurt, bread, noodles, a confection, a cracker, a seasoning powder, or a spread.

6. The method of claim 1, further comprising purifying *Elsholtzia rugulosa* Hemsl. honey before it is added to the therapeutic composition.

7. The method of claim 1, the therapeutic composition is administered in a dose sufficient to cause decolonization of the gastric mucosa by the *Helicobacter pylori*.

8. The method of claim 1, wherein the therapeutic composition is in the form of a tablet, granules, a capsule, a powder, a paste, or a liquid.

9. The method of claim 1, wherein the therapeutic composition is administered by ingestion so that the final concentration of the *Elsholtzia rugulosa* Hemsl. honey is between 10 to 100 micrograms of the honey per ml of the composition within the stomach of the subject.

10. The method of claim 1, wherein the therapeutic composition further comprises at least one of a nutrient, a vitamin, a mineral, a food fiber, a polyunsaturated fatty acid, a stabilizer, a sweetener, a taste component, and a flavor.

11. The method of claim 1, wherein the subject has been diagnosed with a peptic ulcer, gastritis, or a gastric cancer.

12. The method of claim 1, wherein the administering is performed by the subject eating or drinking the therapeutic composition.

\* \* \* \* \*